(12) United States Patent
Maeda et al.

(10) Patent No.: US 10,992,857 B2
(45) Date of Patent: Apr. 27, 2021

(54) INPUT CONTROL DEVICE, INPUT CONTROL METHOD, AND OPERATION SYSTEM

(71) Applicant: SONY CORPORATION, Tokyo (JP)

(72) Inventors: Takeshi Maeda, Tokyo (JP); Seiji Wada, Kanagawa (JP); Kana Matsuura, Kanagawa (JP); Tatsumi Sakaguchi, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/611,260

(22) PCT Filed: May 1, 2018

(86) PCT No.: PCT/JP2018/017379
§ 371 (c)(1),
(2) Date: Nov. 6, 2019

(87) PCT Pub. No.: WO2018/211969
PCT Pub. Date: Nov. 22, 2018

(65) Prior Publication Data
US 2020/0162664 A1 May 21, 2020

(30) Foreign Application Priority Data
May 15, 2017 (JP) .............................. JP2017-096199

(51) Int. Cl.
*H04N 5/232* (2006.01)
*A61B 90/00* (2016.01)
*G06F 3/01* (2006.01)

(52) U.S. Cl.
CPC ....... *H04N 5/23218* (2018.08); *A61B 90/361* (2016.02); *A61B 90/37* (2016.02);
(Continued)

(58) Field of Classification Search
None
See application file for complete search history.

(56) References Cited

U.S. PATENT DOCUMENTS

| 2011/0137156 | A1* | 6/2011 | Razzaque | .......... A61B 18/1477 |
| | | | | 600/424 |
| 2013/0235347 | A1* | 9/2013 | Hennessey | .............. G06F 3/013 |
| | | | | 351/210 |

(Continued)

FOREIGN PATENT DOCUMENTS

| JP | 09-028713 A | 2/1997 |
| JP | 10-118015 A | 5/1998 |

(Continued)

OTHER PUBLICATIONS

International Search Report and Written Opinion of PCT Application No. PCT/JP2018/017379, dated Jul. 17, 2018, 11 pages of ISRWO.

*Primary Examiner* — Matthew Yeung
(74) *Attorney, Agent, or Firm* — Chip Law Group

(57) ABSTRACT

The present technology relates to an input control device, an input control method, and an operation system, which enable achievement of a highly flexible input operation without a burden on a user. A target point determination unit determines a target point to be a display reference in an operative field image in a display, on the basis of a user's line-of-sight position with respect to the operative field image displayed in the display and of a characteristic point detected in the operative field image. The present technology can be applied to an input device for an operation system.

9 Claims, 12 Drawing Sheets

(52) U.S. Cl.
CPC ......... *G06F 3/013* (2013.01); *H04N 5/23296* (2013.01); *A61B 2090/368* (2016.02)

(56) References Cited

U.S. PATENT DOCUMENTS

2015/0286070 A1\* 10/2015 Aikawa ................ A61B 3/0091
                                                               351/159.76
2017/0172675 A1\* 6/2017 Jarc ........................ A61B 90/37

FOREIGN PATENT DOCUMENTS

| | | |
|---|---|---|
| JP | 2015-192697 A | 11/2015 |
| JP | 2016-192986 A | 11/2016 |
| WO | 2015/151447 A1 | 10/2015 |

\* cited by examiner

FIG. 8
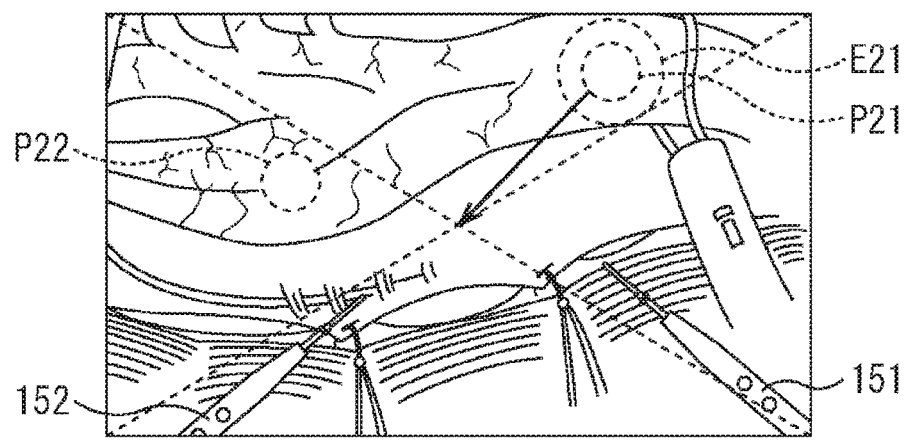
FOOT SWITCH OPERATION
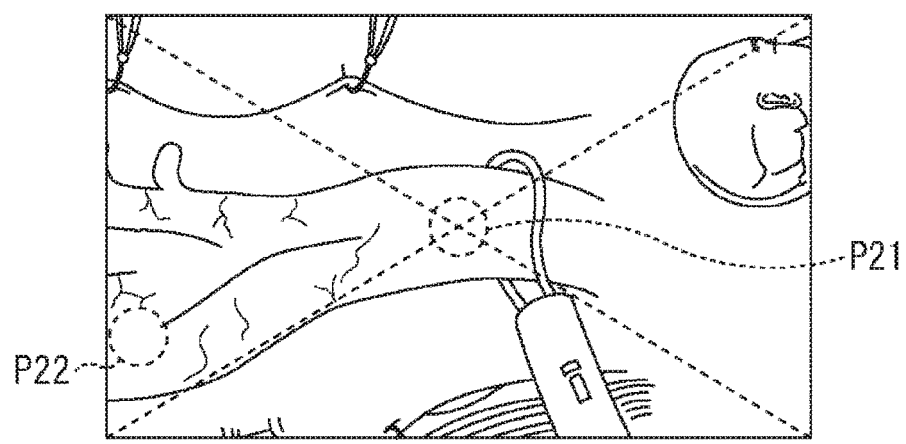

INPUT CONTROL DEVICE, INPUT CONTROL METHOD, AND OPERATION SYSTEM

CROSS REFERENCE TO RELATED APPLICATIONS

This application is a U.S. National Phase of International Patent Application No. PCT/JP2018/017379 filed on May 1, 2018, which claims priority benefit of Japanese Patent Application No. JP 2017-096199 filed in the Japan Patent Office on May 15, 2017. Each of the above-referenced applications is hereby incorporated herein by reference in its entirety.

TECHNICAL FIELD

The present technology relates to an input control device, an input control method, and an operation system, in particular, to an input control device, an input control method, and an operation system that enable achievement of a highly flexible input operation.

BACKGROUND ART

In recent years, it has been proposed for operation systems that screen operations are performed by zoom control of a camera or drive control of a camera arm by a natural user interface (NUI) of a user (operator), such as lines of sight with respect to an operative field image.

Furthermore, conventionally, screen operations have been performed by zoom control of a camera or drive control of a camera arm by regarding, as a target point, a characteristic point of an operation instrument or the like displayed in an operative field image acquired by the camera.

For example, Patent Document 1 discloses that, in an endoscopic operation system, a marker is provided in the vicinity of a tip of a treatment device. Display contents of the marker are changeable by using switches provided at a hand-side of the treatment device, and an endoscope is operated on the basis of the change in the display contents of the marker in an observation image from the endoscope.

A screen operation by a line-of-sight position allows a user to select an arbitrary position in a screen as the target point without using a hand. However, the user has not been able to operate the screen while comprehensively observing an operative field, because the user is inevitably not able to observe positions other than a gaze point.

On the other hand, a screen operation regarding, as the target point, the characteristic point of an operation instrument or the like allow the user to observe a position other than the target point. However, although an operation instrument needs to be moved for observation of a wider operative field, the user has sometimes not been able to perform a desirable screen operation in a case where the movement of the operation instrument is limited, for example, a case where an operation instrument is holding an organ.

CITATION LIST

Patent Document

Patent Document 1: Japanese Patent Application Laid-Open No. 9-28713

SUMMARY OF THE INVENTION

Problems to be Solved by the Invention

Therefore, it is desirable that the target point used for a screen operation can be switched depending on a situation. However, there has been no method for achieving the switching by a simple input operation without a burden on a user.

The present technology has been developed to solve the problems mentioned above, and an object of the present technology is to enable achievement of a highly flexible input operation without a burden on a user.

Solutions to Problems

An input control device according to the present technology includes a target point determination unit that determines a target point to be a display reference in an operative field image in a display on the basis of a user's line-of-sight position with respect to the operative field image displayed in the display and of a characteristic point detected in the operative field image.

An input control method according to the present technology includes a step of determining, by an input control device, a target point to be a display reference in an operative field image in a display on the basis of a user's line-of-sight position with respect to the operative field image displayed in the display and of a characteristic point detected in the operative field image.

An operation system according to the present technology includes a camera that captures an operative field image, a display that displays the operative field image, and an input control device including a target point determination unit that determines a target point to be a display reference in the operative field image in the display on the basis of a user's line-of-sight position with respect to the operative field image displayed in the display and of a characteristic point detected in the operative field image.

In the present technology, a target point to be a display reference in an operative field image in a display is determined on the basis of a user's line-of-sight position with respect to the operative field image displayed in the display and of a characteristic point detected in the operative field image.

Effects of the Invention

The present technology enables achievement of a highly flexible input operation without a burden on a user. Note that the effects described herein are not necessarily limited, and any one of effects described in the present disclosure may be applied.

BRIEF DESCRIPTION OF DRAWINGS

FIG. 8 is a view illustrating an example of target point determination.

MODE FOR CARRYING OUT THE INVENTION

Hereinafter, a mode (hereinafter referred to as embodiment) for carrying out the present disclosure will be described. Note that the description will be made in the following order.

1. Outline of Operation System
2. Functional Configuration Example of Operation System
3. First Example of Operation Control Processing of Operation System
4. Second Example of Operation Control Processing of Operation System <1. Outline of Operation System>

Figure 1:
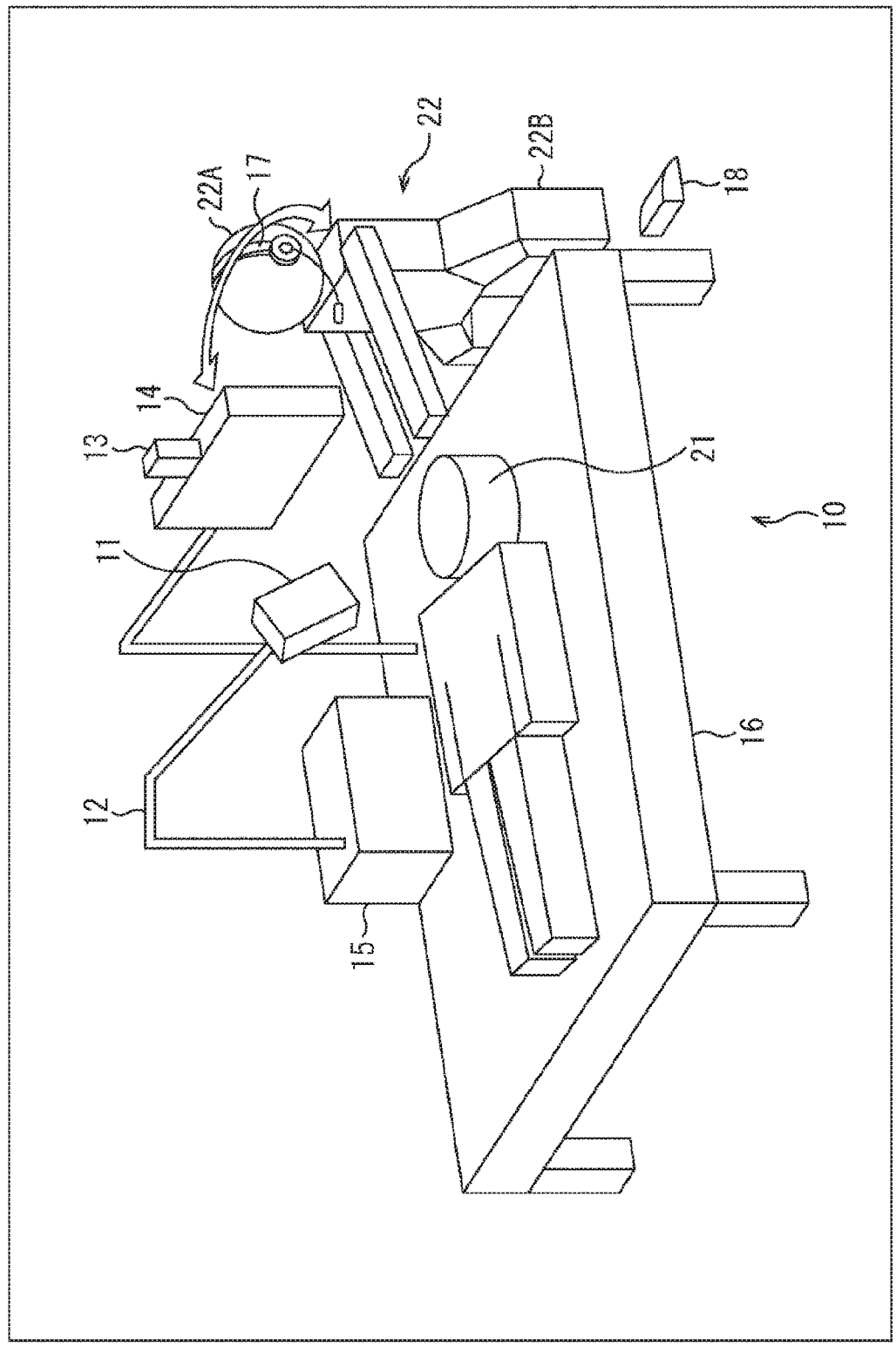
FIG. 1 is a diagram illustrating a configuration example of an operation system, to which the present technology is applied.

FIG. 1 is a block diagram illustrating a configuration example of an operation system, to which the present technology is applied.

An operation system 10 includes an operative field camera 11, a camera arm 12, a motion recognition camera 13, a display 14, a control device 15, an operating table 16, a microphone 17, and a foot switch 18. The operation system 10 is arranged in an operating room or the like and enables treatment such as surgery with reference to an image captured by the operative field camera 11.

The operative field camera 11 (an image capturing device for operation) is a modality device, such as a 3D camera, supported by the camera arm 12. The operative field camera 11 captures an image of an operative field and the like of a patient 21 laid on the operating table 16 and transmits a 3D image acquired as a result of the image capturing to the control device 15, as an operative field image. The camera arm 12 supports the operative field camera 11 and controls a position and an angle of the operative field camera 11.

The motion recognition camera 13 is, for example, a 2D camera and is arranged on the display 14. The motion recognition camera 13 captures an image of an operator 22 wearing the microphone 17 on a head 22A. The motion recognition camera 13 transmits a 2D image acquired as a result of the image capturing to the control device 15, as an operator's image.

The display 14 is a 3D display having a relatively small screen and is arranged relatively near the operator 22 (in the example of FIG. 1, above the operating table 16 and near the operator 22). The display 14 displays the operative field image and the like transmitted from the control device 15.

The control device 15 sets a control mode of the operation system 10 to a manual operation mode or a hands-free mode. The manual operation mode is a mode to control the operation system 10 on the basis of input (for example, force applied to the camera arm 12 or an operation of an unillustrated control button or the like provided at each unit) by a hand of the operator 22. The hands-free mode is a mode to control the operation system 10, not by using the hand of the operator 22, but on the basis of contactless input by sound, a line of sight, movement or a direction of the head 22A, a gesture, and the like, or input by a leg 22B touching the foot switch 18.

An operation, mainly in a case where the control mode is in the hands-free mode, will be described hereinafter.

The control device 15 recognizes movement or a direction of the head 22A by detecting a position of the head 22A in the operator's image transmitted from the motion recognition camera 13. Furthermore, the control device 15 detects a direction of a line of sight of the operator 22 from the operator's image and, on the basis of a direction of the line of sight, recognizes a position of a line of sight on a screen of the display 14.

Note that, in the operation system 10, the line of sight is detected by using the operator's image captured by the motion recognition camera 13. However, the operator 22 may wear glasses equipped with a line-of-sight detection device, and the line-of-sight detection device may detect the line of sight.

Furthermore, in the operation system 10, movement or a direction of the head 22A is detected from the operator's image, because a distance between the motion recognition camera 13 and the operator 22 is short. However, the operator 22 may wear a marker, and the movement or the direction of the head 22A may be detected from a position of the marker in the operator's image.

The control device 15 receives sound transmitted from the microphone 17 and recognizes the sound. The control device 15 receives an operation signal which is transmitted from the foot switch 18 and shows an operation on the foot switch 18, and, on the basis of the operation signal, recognizes content of the operation on the foot switch 18.

Moreover, in a case where the control mode is in the hands-free mode, the control device 15 regards, as input information, movement and a direction of the head 22A, a gesture of the operator 22, information of the line-of-sight position showing a position of a line of sight on the screen of the display 14, a sound recognition result, volume, and operation information showing content of the operation on the foot switch 18. The control device 15 recognizes a command from the operator 22 and a state of the operator 22, on the basis of the input information.

The control device 15 permits the command from the operator 22 according to a state of the operator 22. According to the permitted command, the control device 15 controls image capturing with the operative field camera 11, controls a drive of the camera arm 12, controls a display of the display 14, or changes the control mode.

The microphone 17 is worn on the head 22A of the operator 22. The microphone 17 acquires a surrounding sound including voice of the operator 22 and transmits the sound to the control device 15.

The foot switch 18 is arranged around the operator 22 and operated by the touch by the leg 22B of the operator 22. The foot switch 18 transmits, to the control device 15, the operation signal showing the operation by the leg 22B of the operator 22.

In the operation system 10 configured as above, the operator 22 lays the patient 21 on the operating table 16 and performs treatment such as surgery while checking the operative field image and the like displayed in the display 14.

Furthermore, the operator 22 performs contactless input or input by a touch by a foot, when changing the control mode, an image capture condition of the operative field camera 11, a position and an angle of the operative field camera 11, a display of the display 14, or the like. Therefore, the operator 22 can perform input while holding an unillustrated operation instrument. Therefore, the operator 22 does not require sterilization treatment each time performing input.

Note that any method can be adopted for the detection of the line of sight, for the detection of the movement or the direction of the head 22A of the operator 22 and the gesture of the operator 22, and for acquisition of the sound. For example, the line-of-sight detection device and the microphone 17 may not necessarily be a wearable device.

(Examples of Appearance Configuration and Screen Operation of Foot Switch)

Figure 2:
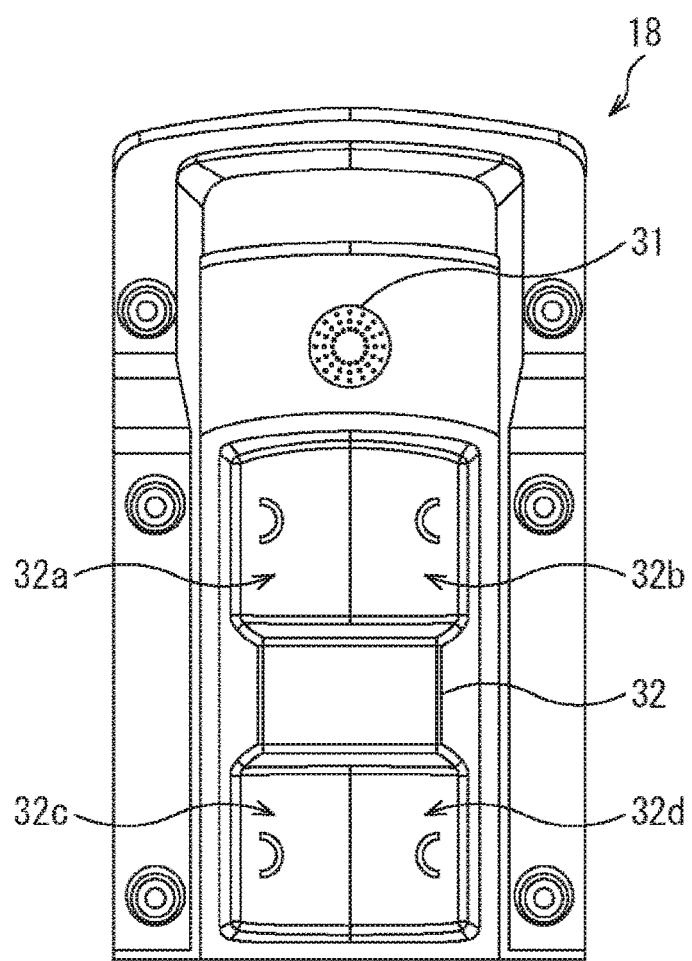
FIG. 2 is a top view illustrating a configuration example of appearance of a foot switch.

FIG. 2 is a top view illustrating a configuration example of appearance of the foot switch 18.

The foot switch 18 includes, as an operation input part, a lever 31 and a treading part 32.

The lever 31 is configured as a so-called joystick and receives operation input by the leg 22B. The lever 31 is used for, for example, positioning of the operative field camera 11 in the manual operation mode.

The treading part 32 is generally configured as a physical button and receives the operation input by the leg 22B. The treading part 32 is used to control each part of the operation system 10. In the present embodiment, an operation mode is set according to movement of the operator 22 and a position of the treading part 32 stepped on by the leg 22B. Then, according to the set operation mode, the operative field camera 11 and the camera arm 12 are controlled, by which a screen operation of the operative field image displayed in the display 14 is performed.

Figure 3:
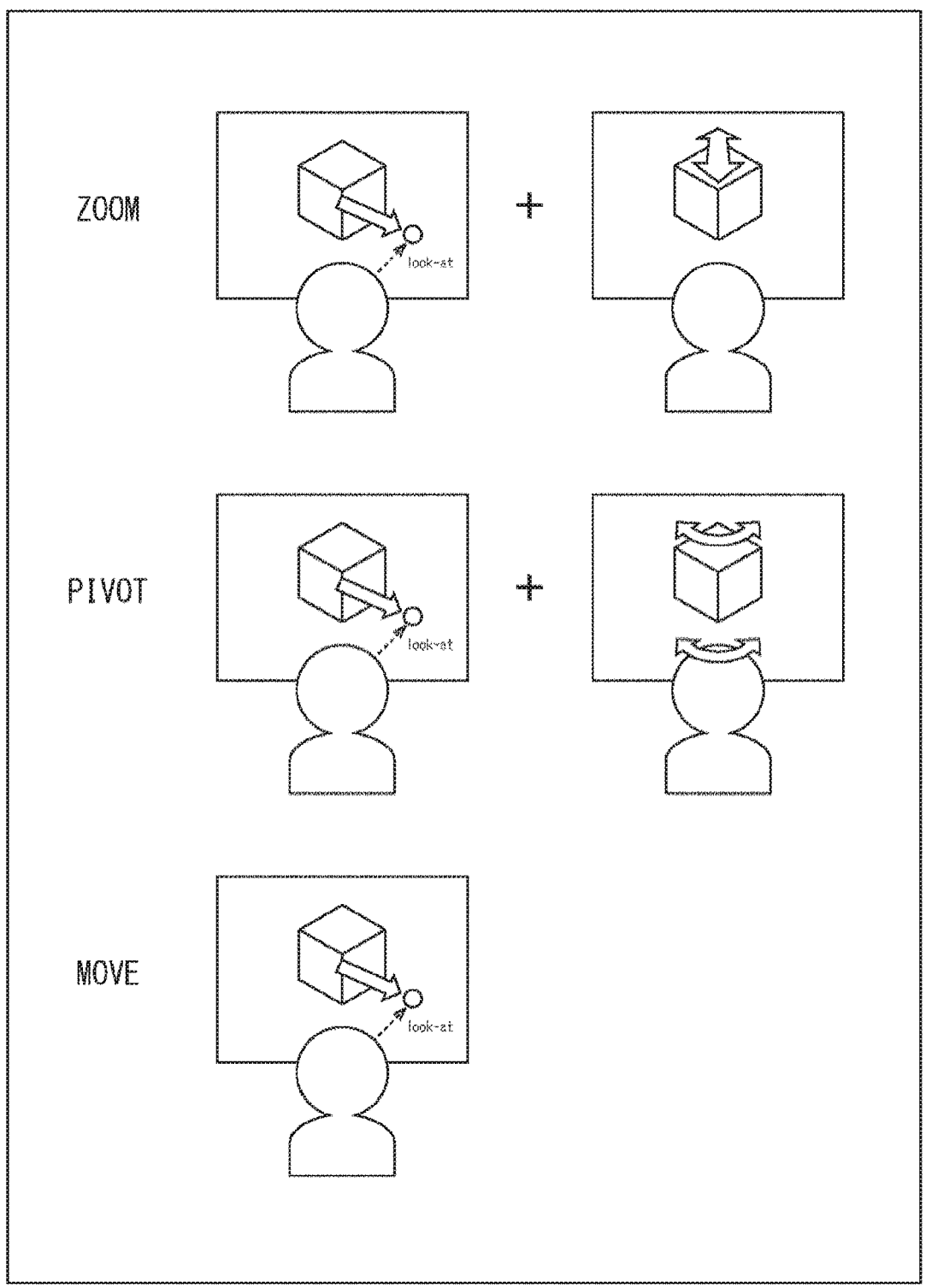
FIG. 3 is a diagram illustrating examples of screen operations in the operation system.

For example, if an upper left part 32a or an upper right part 32b of the treading part 32 is stepped on, as illustrated in an upper part of FIG. 3, the operative field image is zoomed in or out while a predetermined target point in the operative field image displayed in the display 14 is moving to a center of the screen (operation mode: ZOOM).

Furthermore, if the head 22A of the operator 22 tilts to the left or right while a lower left part 32c or a lower right part 32d of the treading part 32 is being stepped on, as illustrated in a middle part of FIG. 3, an image capturing angle of the operative field image is changed while the predetermined target point in the operative field image displayed in the display 14 is moving to the center of the screen (operation mode: PIVOT).

Moreover, if the lower left part 32c or a lower right part 32d of the treading part 32 is stepped on, as illustrated in a lower part of FIG. 3, the predetermined target point in the operative field image displayed in the display 14 moves to the center of the screen (operation mode: MOVE).

Note that any operation mode may be set as an operation mode, not limited to each operation of ZOOM, PIVOT, and MOVE, described above.

(Specific Examples of Screen Operation Based on Target Point)

Here, with reference to FIG. 4, specific examples of a screen operation based on the target point will be described.

In the operation system 10, a target point to be a display reference in the operative field image is determined, and drive control of the camera arm 12 is performed sequentially until the target point moves to the center of the screen.

Figure 4:
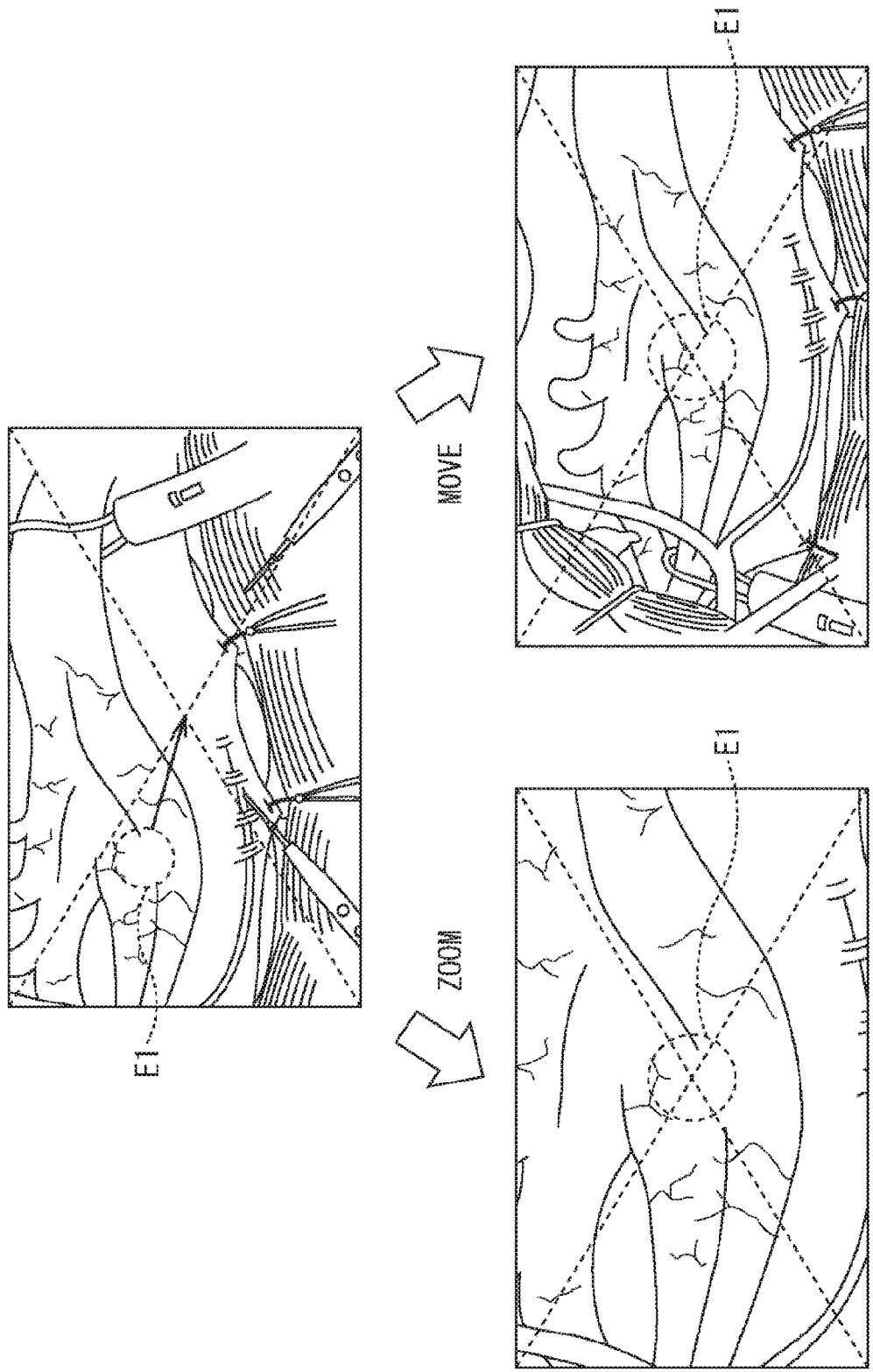
FIG. 4 is a view illustrating specific examples of screen operations based on a target point.

For example, as illustrated in FIG. 4, in a case where a line-of-sight position E1 of the user to the operative field image is regarded as the target point, the camera arm 12 performs a following motion so that the line-of-sight position E1 is positioned at the center of the screen. At this time, the camera arm 12 performs the following motion not by the screen operation described with reference to FIG. 3. For example, in the ZOOM operation, the camera arm 12 performs the following motion while the operative field image is being zoomed in, so that the line-of-sight position E1 is positioned at the center of the image. Meanwhile in the MOVE operation, the camera arm 12 performs the following motion so that, simply, the line-of-sight position E1 is positioned at the center of the screen.

<2. Functional Configuration Example of Operation System>

Figure 5:
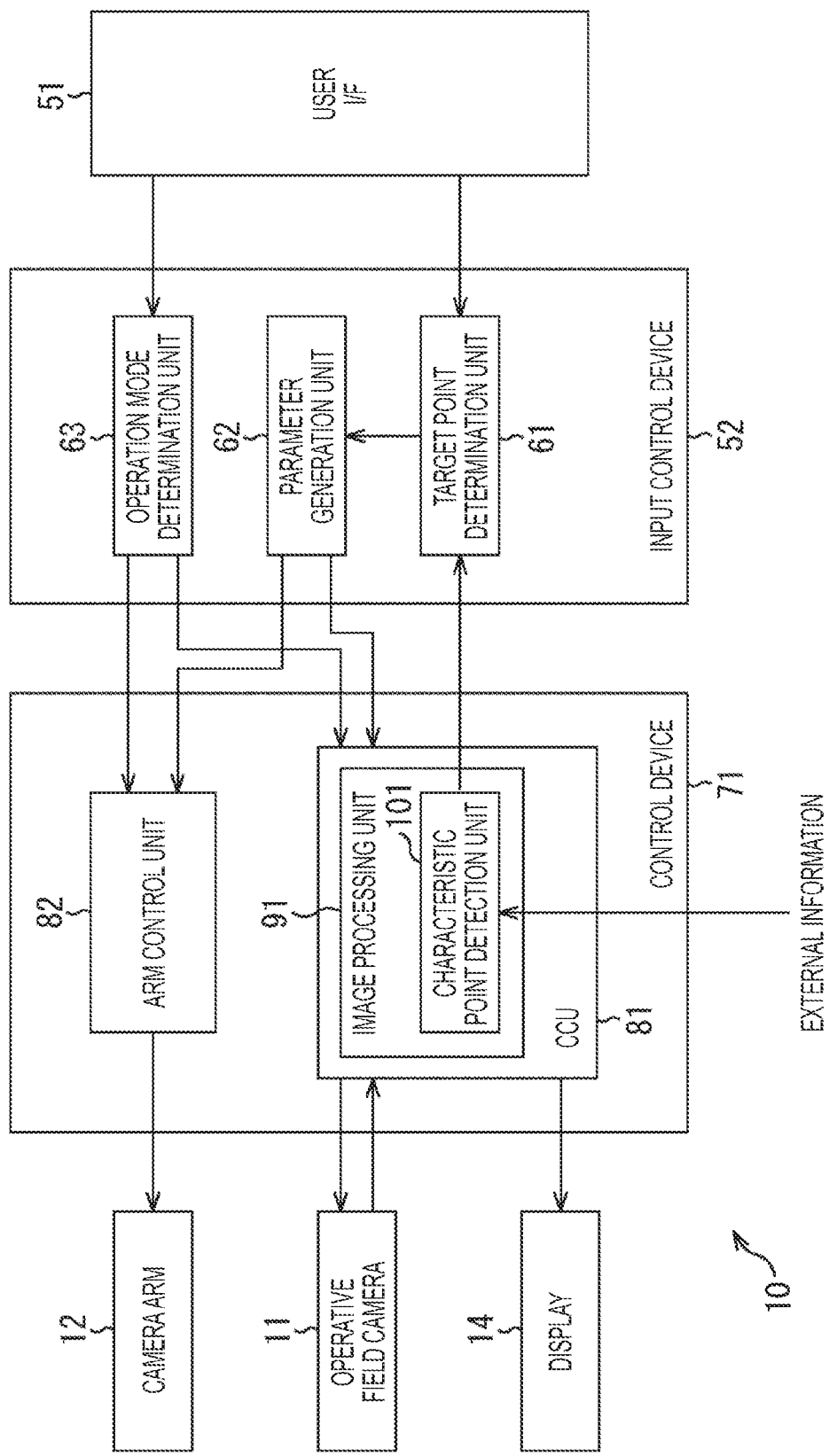
FIG. 5 is a block diagram illustrating a functional configuration example of the operation system.

FIG. 5 is a block diagram illustrating a functional configuration example of the operation system 10.

The operation system 10 illustrated in FIG. 5 includes the operative field camera 11, the camera arm 12, the display 14, a user interface (I/F) 51, an input control device 52, and a control device 71.

The user I/F 51 includes various input devices in the operation system 10. The user (operator 22) can input various kinds of information or instructions into the operation system 10 via the user I/F 51. The input information indicating content of the input into the user I/F 51 is provided to the input control device 52.

The user I/F 51 includes the motion recognition camera 13, the microphone 17, and the foot switch 18. The motion recognition camera 13 provides the input control device 52 with the operator's image, which is the captured image of the operator, as input information. Furthermore, the foot switch 18 provides the input control device 52 with operation information showing content of the operation by the operator 22, as input information.

Moreover, the user I/F 51 may include a device, for example, a glasses-type wearable device or a head mounted display (HMD), which is worn by the user, and various kinds of input may be performed according to the gesture or the line of sight of the user detected by these devices.

The input control device 52, on the basis of the input information from the user I/F 51, generates control information that the control device 71 will use to control the operative field camera 11 and the camera arm 12, and then provides the control information to the control device 71.

The input control device 52 includes a target point determination unit 61, a parameter generation unit 62, and an operation mode determination unit 63.

The target point determination unit 61 determines, on the basis of the input information provided from the user I/F 51, the target point to be the display reference in the operative field image in the display 14.

Specifically, the target point determination unit 61 detects the direction of the line of sight of the operator 22 from the operator's image provided as the input information by the user I/F 51, and, on the basis of the direction, recognizes the line-of-sight position on the screen of the display 14. Furthermore, the target point determination unit 61 acquires information which is provided by the control device 71 and shows a characteristic point detected in the operative field image captured by the operative field camera 11. Then, the target point determination unit 61 determines any one of the line-of-sight position of the operator 22 or the characteristic point detected in the operative field image, as the target point to be the display reference in the display 14.

The parameter generation unit 62 generates a parameter to control the operative field camera 11 and the camera arm 12, in order to display the operative field image in the display 14 with reference to the target point determined by the target point determination unit 61. The parameter generated by the parameter generation unit 62 is provided to the control device 71 as control information.

By detecting the position of the head 22A in the operator's image provided as the input information by the user I/F 51, the operation mode determination unit 63 recognizes movement of the operator 22, such as movement or a direction of the head 22A. The operation mode determination unit 63 determines, on the basis of a recognition result of the movement of the operator 22, an operation mode (ZOOM, PIVOT, or MOVE) being instructed by the operator 22 and provides the control device 71 with operation mode information showing the operation mode, as control information.

On the basis of the control information provided by the input control device 52, the control device 71 controls operation of the operative field camera 11 and the camera arm 12, as well as a display of the operative field image in the display 14.

The control device 71 includes a camera control unit (CCU) 81 and an arm control unit 82.

The CCU 81 controls an operation of the operative field camera 11 and the display 14.

Specifically, on the basis of the parameter from the parameter generation unit 62 and the operation mode information from the operation mode determination unit 63, the CCU 81 performs zoom control or focus control of the operative field camera 11. In the zoom control of the operative field camera 11, either optical zoom control or digital zoom control may be performed.

The CCU 81 includes an image processing unit 91.

The image processing unit 91 performs various kinds of image processing for image display on the operative field image captured by the operative field camera 11 and provides the display 14 with the operative field image. Moreover, the image processing unit 91 includes a characteristic point detection unit 101.

The characteristic point detection unit 101 detects a predetermined characteristic point from the operative field image captured by the operative field camera 11 and provides the input control device 52 with the information showing the characteristic point. For example, the characteristic point detection unit 101 detects a characteristic area in the operative field image, such as a portion of an operation instrument used in an operation, or an organ or blood vessel which is a biological tissue in an operative site. Note that the characteristic point detection unit 101 may detect the characteristic point by referring to, for example, a computed tomography (CT) image or external information such as information from a navigation system for operation.

On the basis of the parameter from the parameter generation unit 62 and the operation mode information from the operation mode determination unit 63, the arm control unit 82 performs drive control of the camera arm 12.

Note that, in the example in FIG. 5, the input control device 52 may be configured integrally with either the user I/F 51 or the control device 71.

With the configuration above, in the operation system 10, the screen operation is performed with the user's line-of-sight position or the characteristic point detected in an image of an operative site, regarded as the target point.

In a conventional operation system, a screen operation by a line-of-sight position allows a user to select an arbitrary position in a screen as a target point without using a hand. However, the user has not been able to operate the screen while comprehensively observing an operative field, because the user is inevitably not able to observe positions other than a gaze point.

On the other hand, a screen operation regarding, as the target point, the characteristic point of an operation instrument or the like allow the user to observe a position other than the target point. However, although an operation instrument needs to be moved for observation of a wider operative field, the user has sometimes not been able to perform a desirable screen operation in a case where the movement of the operation instrument is limited, for example, a case where an operation instrument is holding an organ.

Therefore, it is desirable that the target point used for the screen operation can be switched depending on a situation.

However, in some cases, there is a possibility that the switching of the target point by an input operation using a button or the like becomes a burden on the users. Especially, in a case where there is a plurality of candidates for the target point, switching of the target point requires to be achieved by a simpler input operation in order to avoid users' confusion.

Therefore, operation control processing of the operation system 10, which achieves switching of the target point to be used for the screen operation by a simple input operation without a burden on the users, will be described hereinafter.

<3. First Example of Operation Control Processing of Operation System>

First, a first example of operation control processing of the operation system 10 will be described with reference to a flowchart in FIG. 6. In this example, processing in a case where the MOVE operation is performed as the operation mode will be described.

In Step S11, the target point determination unit 61 determines whether or not the line of sight of the operator 22 has been detected from the operator's image from the user I/F 51. The processing of Step S11 is repeated until the line of sight of the operator 22 is detected. Then, when it is determined that the line of sight of the operator 22 has been detected, the processing proceeds to Step S12.

In Step S12, the characteristic point detection unit 101 detects the characteristic point from the operative field image captured by the operative field camera 11.

In Step S13, the target point determination unit 61 determines whether or not the characteristic point detected in the operative field image by the characteristic point detection unit 101 and the line-of-sight position of the operator 22 have matched with each other. When it is determined in Step S13 that the characteristic point and the line-of-sight position of the operator 22 have matched with each other, the processing proceeds to Step S14.

In Step S14, the target point determination unit 61 selects, as a target point candidate, the characteristic point that has matched with the line-of-sight position of the operator 22.

Meanwhile, the processing proceeds to Step S15 in a case where it is determined in Step S13 that the characteristic point and the line-of-sight position of the operator 22 have not matched with each other.

In Step S15, the target point determination unit 61 selects the line-of-sight position as the target point candidate.

In Step S16, the operation mode determination unit 63 determines whether or not the foot switch 18 has been operated. Here, the operation of the foot switch 18 is the operation to instruct an operation mode. For a period until the foot switch 18 is operated (for a period until an operation mode is instructed), the processing in Steps S13 to S15 is repeated, and selection of the target point candidate is repeated. Then, when it is determined that the foot switch 18 has been operated, the processing proceeds to Step S17.

In Step S17, triggered by the operation of the foot switch 18, the target point determination unit 61 determines, as the target point, the characteristic point or the line-of-sight position, whichever is selected as the target point candidate.

In Step S18, the parameter generation unit 62 generates the parameter to display the operative field image in the display 14 with reference to the target point determined by the target point determination unit 61.

In Step S19, the CCU 81 and the arm control unit 82 perform zoom control of the operative field camera 11 and drive control of the camera arm 12, on the basis of the parameter generated by the parameter generation unit 62 and the operation mode information showing the MOVE operation, the operation mode information being provided by the operation mode determination unit 63.

For example, the CCU 81 controls the drive of the camera arm 12 by calculating an amount of the drive of the camera arm 12, the amount necessary to move the target point to the center of the screen, on the basis of information of an angle of view or the like of the operative field camera 11.

In Step S20, the operation mode determination unit 63 determines whether or not the foot switch 18 is being operated. While the foot switch 18 is being operated, the processing in Steps S16 and S17 is repeated. In this example, the MOVE operation is performed continuously with reference to the target point.

Meanwhile, in a case where is determined in Step S20 that the foot switch 18 is not being operated, the zoom control of the operative field camera 11 and the drive control of the camera arm 12 are stopped, and the processing is ended.

Figure 7:
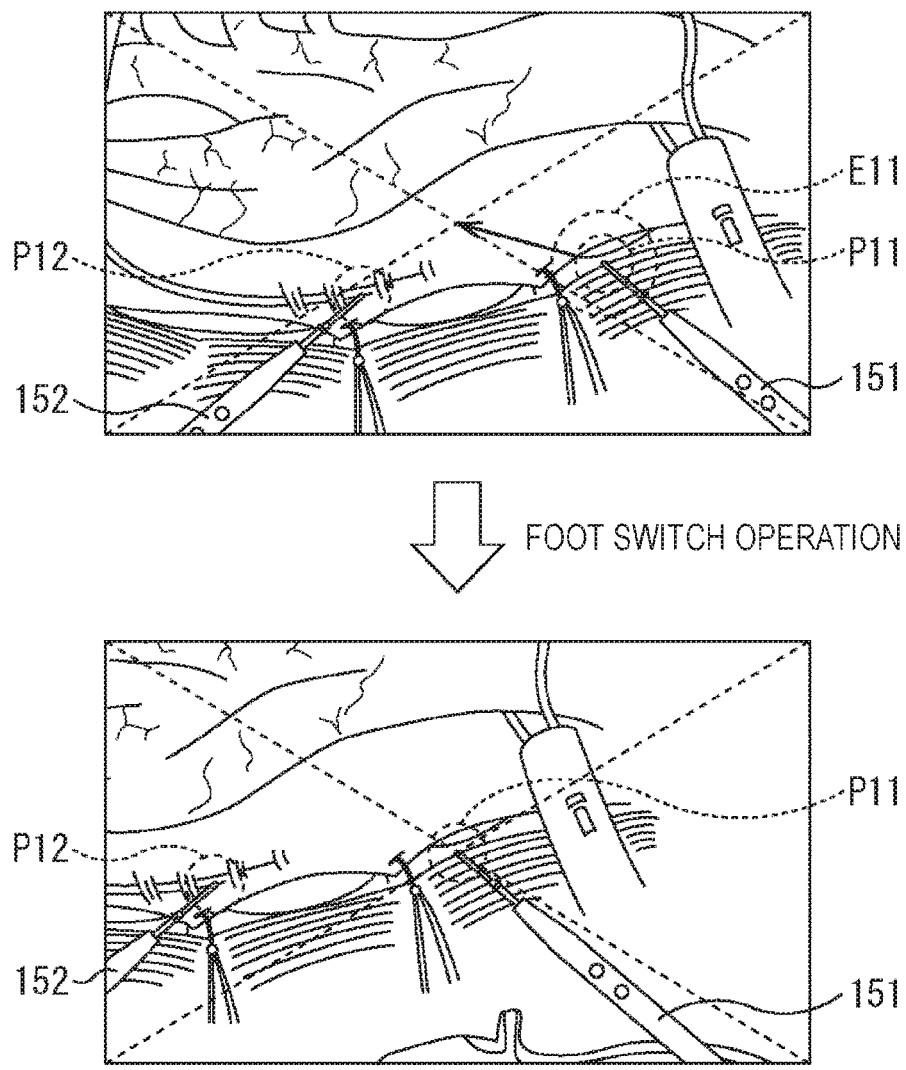
FIG. 7 is a view illustrating an example of target point determination.

For example, in the operative field image illustrated in the upper part of FIG. 7, a tip of an operation instrument 151 is detected as a characteristic point P11, and a tip of an operation instrument 152 is detected as a characteristic point P12. Here, in a case where the operator 22 wishes to select the characteristic point P11 as the target point from the characteristic point P11 and the characteristic point P12, a line-of-sight position E11 of the operator 22 and the characteristic point P11 match with each other by the operator 22 gazing at the characteristic point P11.

Then, by the operator 22 in this state operating the foot switch 18 to instruct the MOVE operation, as illustrated in the lower part of FIG. 7, the characteristic point P11 (the tip of the operation instrument 151) is positioned at the center of the operative field image.

Furthermore, in the operative field image illustrated in the upper part of FIG. 8, a portion of a blood vessel is detected as a characteristic point P21, and another portion of the blood vessel is detected as a characteristic point P22. Here, in a case where the operator 22 wishes to select the characteristic point P21 as the target point from the characteristic point P21 and the characteristic point P22, a line-of-sight position E21 of the operator 22 and the characteristic point P21 match with each other by the operator 22 gazing at the characteristic point P21.

Then, by the operator 22 in this state operating the foot switch 18 to instruct the MOVE operation, as illustrated in the lower part of FIG. 8, the characteristic point P21 is positioned at the center of the operative field image.

Note that, in the example in FIG. 8, a CT image or external information such as information from a navigation system for operation may be used to detect the characteristic point of the blood vessel, organ, and the like.

Furthermore, in the examples in FIGS. 7 and 8, the target point is determined by the foot switch 18 operated in a state that one of the characteristic points is selected as the target point candidate by the line-of-sight position. However, the line-of-sight position itself can be determined as the target point in the processing described above.

For example, even in a case where there are selectable characteristic points as illustrated in the examples in FIGS. 7 and 8, the line-of-sight position itself is selected as the target point candidate by operating the foot switch 18 with the characteristic points not being selected by the line-of-sight position. Furthermore, the line-of-sight position itself may be determined as the target point by operating the foot switch 18 with the characteristic points not being detected in the operative field image.

By using the processing described above, triggered by the user's operation, any one of the user's line-of-sight position with respect to the operative field image or the characteristic point detected in the operative field image is determined as the target point. Thus, switching of the target point to be used for the screen operation can be achieved by a simple input operation without a burden on the user.

Note that, in the processing described above, information showing a point to be the target point candidate such as the user's line-of-sight position or the characteristic point of the operation instrument may be either always or not always displayed in the operative field image. Especially, there is a possibility that presentation of information irrelevant to an operative procedure in the operative field image used for an operation hinders progress of the operation. Therefore, in some cases, such information is preferable not to always be displayed.

Figure 9B:
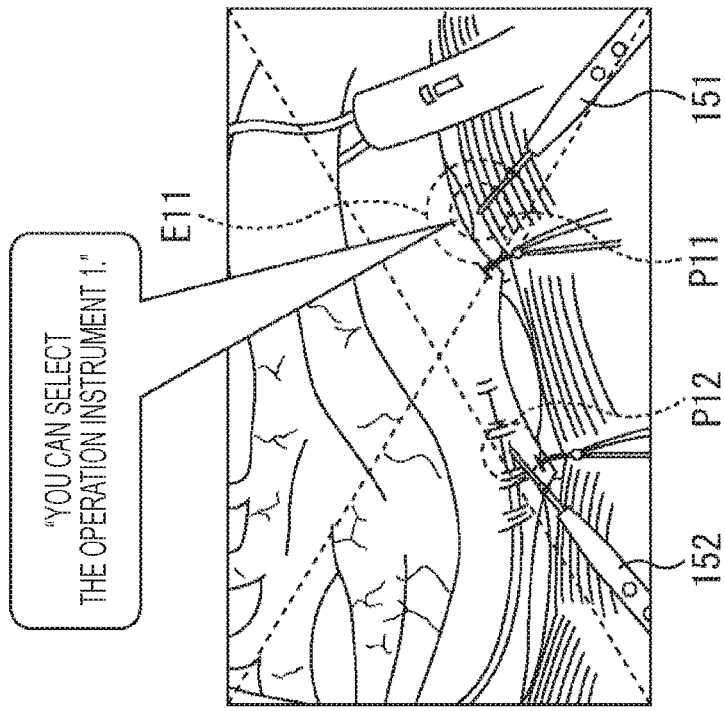
FIGS. 9A and 9B are views describing an example of a feedback of a target point candidate to a user.
Figure 9A:
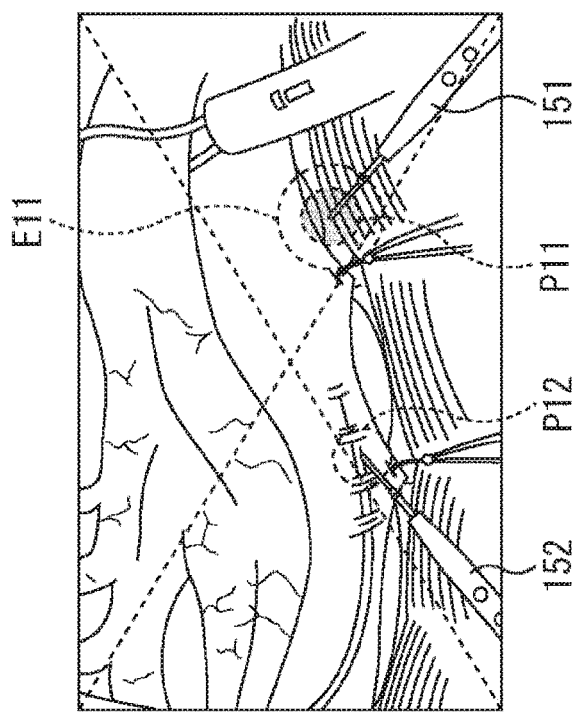

FIGS. 9A and 9B are views illustrating examples of a feedback of the point to be the target point candidate to the user.

In each operative field image in FIGS. 9A and 9B, the tip of the operation instrument 151 is detected as the characteristic point P11, and the tip of the operation instrument 152 is detected as the characteristic point P12. In a case where any one of the characteristic points has matched with the line-of-sight position E11 of the user, the matching is fed back to the user.

In the example in FIG. 9A, an area of the characteristic point P11 is displayed with emphasis by the line-of-sight position E11 matching with the characteristic point P11. Furthermore, in the example in FIG. 9B, a voice message saying, for example, "You can select the operation instrument 1." is output by the line-of-sight position E11 matching with the characteristic point P11. With these methods, the point to be the target point candidate can be recognized by the user without hindering progress of the operation.

Note that a method of feedback to the user is not limited to the methods exemplified in FIGS. 9A and 9B.

Furthermore, in the processing described above, processing to forcibly stop the operation control processing may be performed from a view point of a fail-safe operation.

For example, there may be a case where, while the tip of the operation instrument is determined as the target point, and the camera arm 12 performs the following motion on the basis of the target point, the tip of the operation instrument is suddenly framed out of the operative field image.

Figure 10:
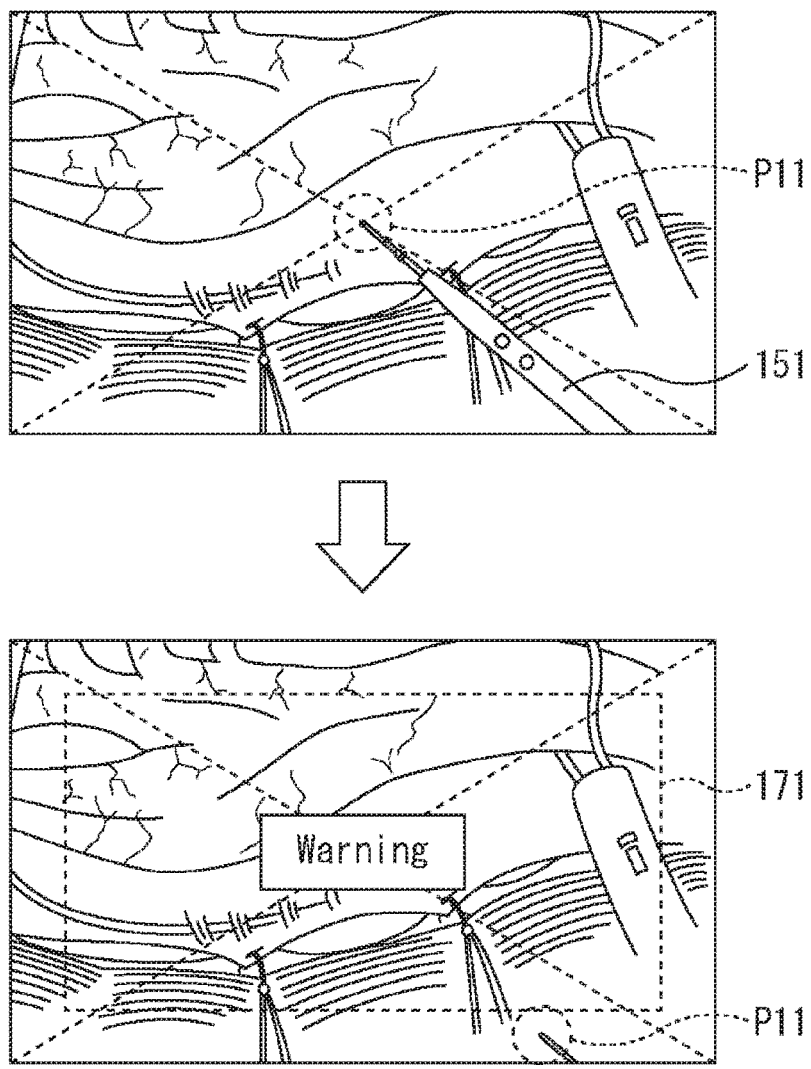

Therefore, as illustrated in the upper part of FIG. 10, after the tip of the operation instrument 151 (characteristic point P11) is determined as the target point, coordinates of the characteristic point P11 on the screen are always monitored.

Then, as illustrated in the lower part of FIG. 10, it is determined whether or not the coordinates of the characteristic point P11 are positioned within a rectangular area 171 that is set on the screen and has a size predetermined with reference to the center of the screen. In a case where the coordinates of the characteristic point P11 are determined not to be positioned within the rectangular area 171, the operation control processing is forced to stop.

Moreover, the operation control processing may be forced to stop also in a case where the user's line-of-sight position selecting the target point candidate becomes unable to be detected during the following motion by the camera arm 12.

<4. Second Example of Operation Control Processing of Operation System>

Next, a second example of the operation control processing of the operation system 10 will be described with reference to a flowchart in FIG. 11.

Figure 6:
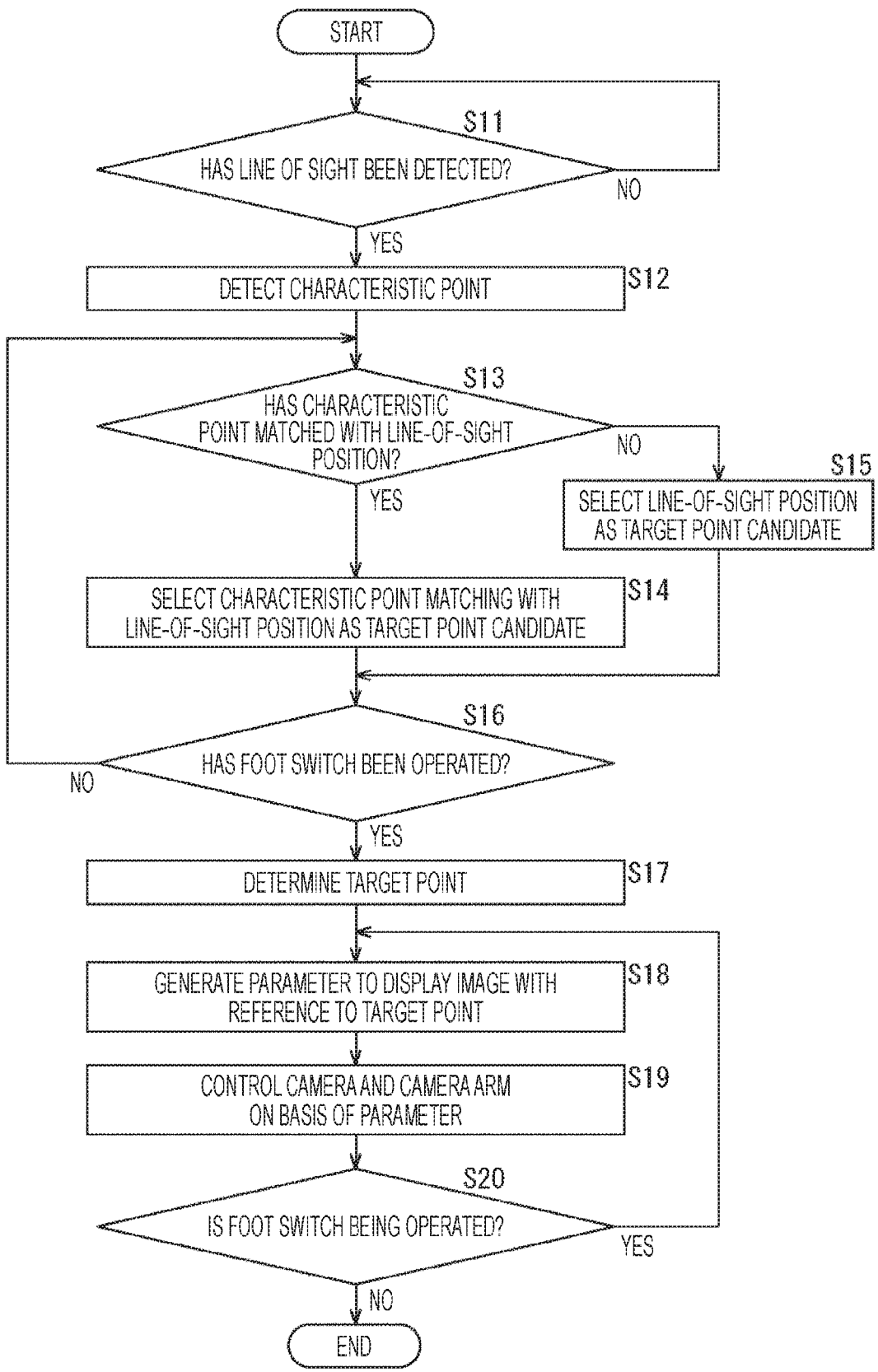
FIG. 6 is a flowchart describing a first example of operation control processing.
Figure 11:
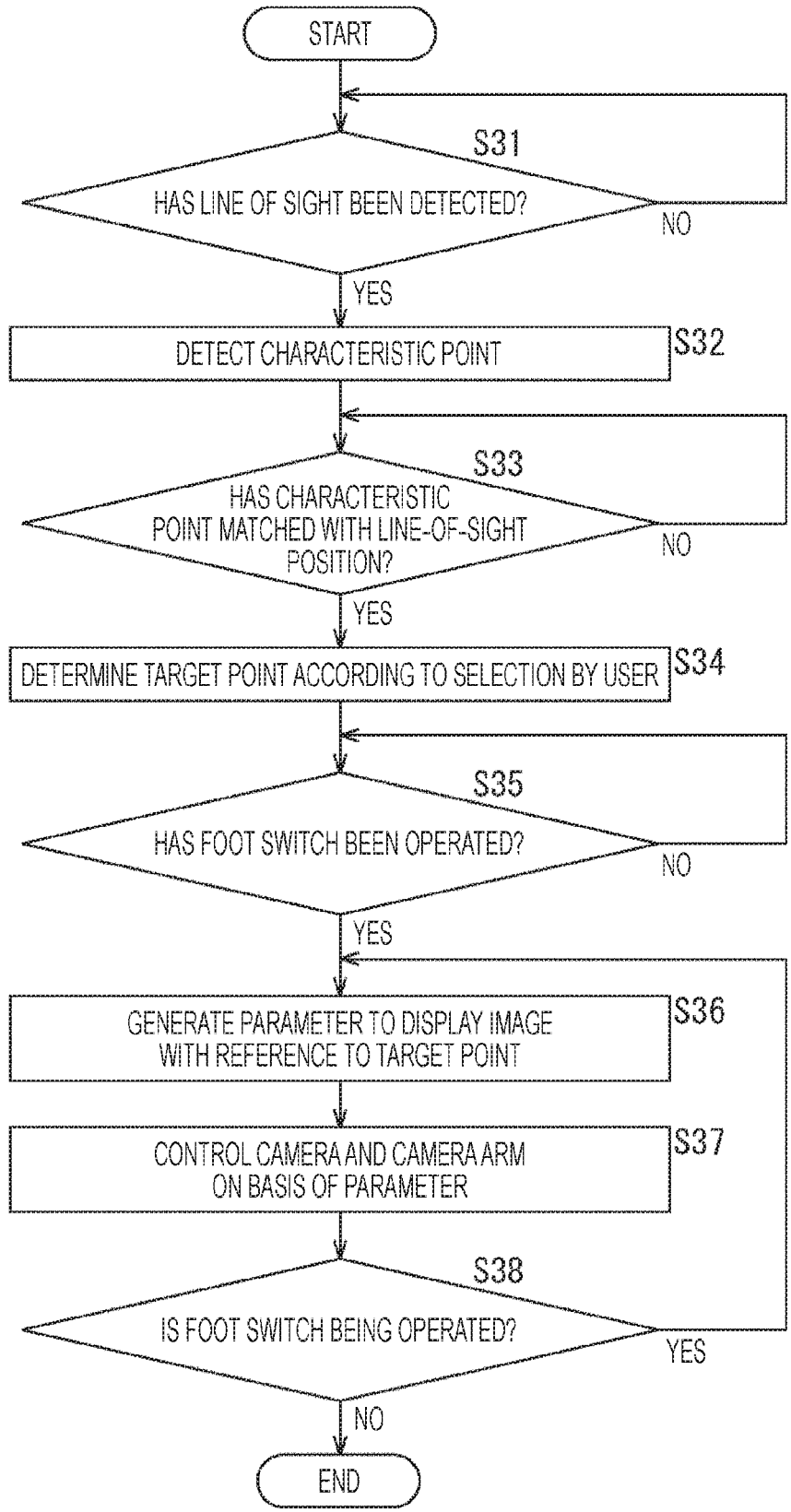

Note that description of the processing in Steps S31, S32, and S36 to S38 in the flowchart in FIG. 11 will be omitted, because the processing is similar to the processing in Steps S11, S12, and S18 to S20 in the flowchart in FIG. 6.

Furthermore, in the processing in FIG. 11, it is assumed that any one of the characteristic point in the operative field image or the user's line-of-sight position is previously set as the target point.

In Step S33, the target point determination unit 61 determines whether or not the characteristic point detected in the operative field image by the characteristic point detection unit 101 and the line-of-sight position of the operator 22 has matched with each other. The processing of Step S33 is repeated until the characteristic point and the line-of-sight position of the operator 22 match with each other. Then, when it is determined in Step S33 that the characteristic point and the line-of-sight position of the operator 22 have matched with each other, the processing proceeds to Step S34.

In Step S34, according to a selection by the user (operator 22), the target point determination unit 61 determines, as the target point, any one of the characteristic point matching with the line-of-sight position of the operator 22 or the line-of-sight position of the operator 22.

Figure 12:
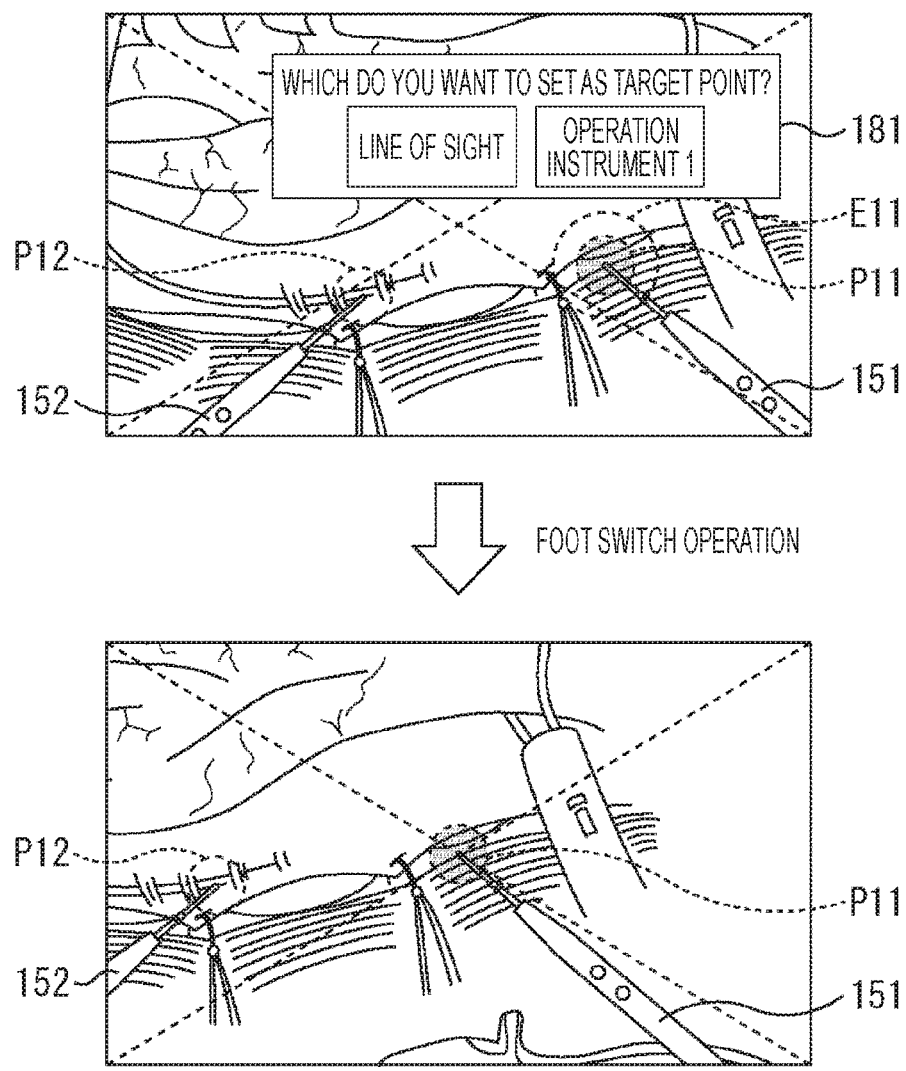

For example, in the operative field image illustrated in the upper part of FIG. 12, the tip of the operation instrument 151 is detected as the characteristic point P11, and the tip of the operation instrument 152 is detected as the characteristic point P12. Here, it is assumed that the line-of-sight position E11 of the operator 22 is previously set as the target point. If the operator 22 in this state gazes at the characteristic point P11, the line-of-sight position E11 of the operator 22 and the characteristic point P11 match with each other.

At this time, a pop-up window 181 appears in the operative field image. The pop-up window 181 prompts the operator 22 to select which one, the line-of-sight position E11 or the characteristic point P11, is determined as the target point. The pop-up window 181 includes a button to determine the line-of-sight position E11 as the target point and a button to determine the characteristic point P11 (the tip of the operation instrument 151) as the target point. A selected state of these buttons is toggled by, for example, operation of the foot switch 18, and either of the buttons is finally selected.

In the example in FIG. 12, it is selected that the characteristic point P11 is determined as the target point (the target point is switched from the line-of-sight position E11 to the characteristic point P11), and the characteristic point P11 (the tip of the operation instrument 151) is positioned at the center of the operative field image, as illustrated in the lower part of FIG. 12.

Note that, in the example in FIG. 12, the pop-up window 181 appears to prompt the operator 22 to select which one, the line-of-sight position E11 or the characteristic point P11, is determined as the target point. However, not limited to this, the operator 22 may be notified of the prompt by, for example, sound.

Furthermore, by operation of the foot switch 18, which one, the line-of-sight position E11 or the characteristic point P11, is determined as the target point is selected. However, not limited to this, which one, the line-of-sight position E11 or the characteristic point P11, is determined as the target point may be selected by using another method.

Thus, after the target point is determined, in Step S35, the target point determination unit 61 determines whether or not the foot switch 18 has been operated to instruct an operation mode. The processing of Step S35 is repeated until the foot switch 18 is operated. Then, when it is determined that the foot switch 18 has been operated, the processing proceeds to Step S36.

In and after Step S36, zoom control of the operative field camera 11 and drive control of the camera arm 12 are performed according to the instructed operation mode.

By using the processing described above, when the characteristic point detected in the operative field image and the user's line-of-sight position with respect to the operative field image match with each other, either the characteristic point or the user's line-of-sight position, whichever is selected by the user's operation, is determined as the target point. Therefore, switching of the target point to be used for the screen operation can be achieved by a simple input operation without a burden on the user.

Note that, in the processing described above, a display or notification to prompt the operator 22 to select which one, the line-of-sight position or the characteristic point, is determined as the target point, in other words, query about switching of the target point, is performed when the characteristic point and the line-of-sight position of the operator 22 match with each other. However, the query about switching of the target point may be performed at any timing, such as at a timing specified by the operator 22 or at a predetermined time interval.

Furthermore, the query about switching of the target point may be performed in the operation control processing described with reference to the flowchart in FIG. 6. In this case, for example, when three points, which are the user's line-of-sight position, the operation instrument, and the biological tissue such as a blood vessel, are matched with one another, the query about switching the target point is performed.

In the above, a configuration to move the target point to be the display reference in the operative field image to the center of the screen is described. However, not limited to this, the target point may be moved to any position on the screen.

Note that, in the operation system described above, an object to be controlled on the basis of the input information is not limited to the operative field camera 11 and the camera arm 12, and any other configuration may be used.

In the above, an example is described in which the technology according to the present disclosure is applied to the operation system that uses the operative field camera. However, the system to which the technology according to the present disclosure may be applied is not limited to this example. For example, the technology according to the present disclosure may be applied to an endoscope system or a microscopic operation system.

Note that a hardware configuration for the control device 71 or the input control device 52 can be configured with an information processing device including a circuit that can achieve a function of the control device 71 or the input control device 52. The information processing device constituting the control device 71 or the input control device 52 includes, for example, a central processor unit (CPU), a read only memory (ROM), a random access memory (RAM), and a storage device. The function of the control device 71 or the input control device 52 is achieved by the CPU developing and running, on the RAM, a program previously recorded in the ROM or the storage device, for example.

Moreover, the information processing device may include an external bus such as a host bus, a bridge, and a peripheral component interconnect/interface (PCI) bus, an interface, an input device, an output device, a drive, a connection port, and a communication device. These components may be interconnected. Each of the components described above may include a general-purpose member or hardware dedicated to a function of each component. Therefore, a configuration of hardware to be used can be appropriately changed according to a technical level at a time of implementing the present embodiment.

Note that a computer program to achieve each function of the information processing devices, which constitute the operation system according to the present embodiment as described above, can be manufactured and mounted on a personal computer, or the like. Furthermore, a recording medium, which stores such a computer program and is readable by a computer, can also be provided. The recording medium is, for example, a magnetic disk, an optical disc, a magneto-optical disk, or a flash memory. Furthermore, the computer program described above may be distributed via, for example, a network, without using the recording medium. Furthermore, the number of computers to run the computer program is not especially limited. For example, a plurality of computers (for example, a plurality of servers) may be linked one another to run the computer program.

Furthermore, the embodiment of the present technology is not limited to the embodiment described above and can be changed in various ways without departing from the gist of the present technology.

Moreover, the present technology can have the following configurations.

(1)
An input control device including
a target point determination unit that determines a target point to be a display reference in an operative field image in a display, on the basis of a user's line-of-sight position with respect to the operative field image displayed in the display and of a characteristic point detected in the operative field image.

(2)
The input control device according to (1),
in which the target point determination unit determines any one of the user's line-of-sight position with respect to the operative field image or the characteristic point detected in the operative field image, as the target point.

(3)
The input control device according to (1) or (2),
in which the characteristic point is a point that indicates a portion of an operation instrument, the portion being detected in the operative field image.

(4)
The input control device according to (1) or (2),
in which the characteristic point is a point that indicates a biological tissue in an operative site, the biological tissue being detected in the operative field image.

(5)
The input control device according to any one of (2) to (4),
in which, in a case where the characteristic point detected in the operative field image and the user's line-of-sight position with respect to the operative field image match with each other, the target point determination unit determines, triggered by an operation by the user, the characteristic point as the target point.

(6)
The input control device according to (5),
in which, in a case where the characteristic point detected in the operative field image and the user's line-of-sight position with respect to the operative field image do not match with each other, the target point determination unit determines, triggered by the operation by the user, the user's line-of-sight position as the target point.

(7)
The input control device according to any one of (2) to (4),
in which, in a case where the characteristic point detected in the operative field image and the user's line-of-sight position with respect to the operative field image match with each other, the target point determination unit determines either the characteristic point or the user's line-of-sight position, whichever is selected by the user's operation, as the target point.

(8)
The input control device according to any one of (1) to (7), further including
a parameter generation unit that generates a parameter to control a mechanism that is driven to display the operative field image in the display with reference to the determined target point.

(9)
The input control device according to (8), in which
the parameter is a parameter to perform at least one of zoom control of a camera that captures the operative field image or drive control of a camera arm that supports the camera.

(10)
An input control method including
a step of determining, by an input control device, a target point to be a display reference in an operative field image in a display, on the basis of a user's line-of-sight position with respect to the operative field image displayed in the display and of a characteristic point detected in the operative field image.

(11)
An operation system including:
a camera that captures an operative field image;
a display that displays the operative field image; and
an input control device that includes
a target point determination unit that determines a target point to be a display reference in the operative field image in the display, on the basis of a user's line-of-sight position with respect to the operative field image displayed in the display and of a characteristic point detected in the operative field image.

REFERENCE SIGNS LIST

10 Operation system
11 Operative field camera
12 Camera arm
13 Motion recognition camera
14 Display
15 Control device
17 Microphone
18 Foot switch
51 User I/F
52 Input control device
61 Target point determination unit
62 Parameter generation unit
63 Operation mode determination unit
71 Control device 81 CCU
82 Arm control unit
91 Image processing unit
101 Characteristic point detection unit

The invention claimed is:

1. An input control device, comprising:
a target point determination unit configured to:
determine one of:
a user's line-of-sight position with respect to an operative field image matches with a characteristic point in the operative field image, or
the user's line-of-sight position is different from the characteristic point in the operative field image,
wherein the operative field image is displayed on a display screen; and
determine the user's line-of-sight position as a target point, wherein
the target point is a display reference for the operative field image displayed in the display screen, and
the user's line-of-sight position is determined as the target point based on the determination that the user's line-of-sight position with respect to the operative field image is different from the characteristic point in the operative field image; and
circuitry configured to control movement of the determined target point in the operative field image to a center of the display screen.

2. The input control device according to claim 1, wherein the characteristic point indicates a portion of an operation instrument, and
the portion is in the operative field image.

3. The input control device according to claim 1, wherein the characteristic point indicates a biological tissue in an operative site, and
the biological tissue is in the operative field image.

4. The input control device according to claim 1, wherein the target point determination unit is further configured to determine the characteristic point as the target point based on
a user operation, and
the determination that the user's line-of-sight position with respect to the operative field image matches with the characteristic point in the operative field image.

5. The input control device according to claim 1, wherein the target point determination unit is further configured to determine one of the characteristic point or the user's line-of-sight position as the target point based on
a user selection of the one of the characteristic point or the user's line-of-sight position, and
the determination that the user's line-of-sight position with respect to the operative field image matches with the characteristic point in the operative field image.

6. The input control device according to claim 1, further comprising a parameter generation unit configured to:
generate a parameter; and
control a mechanism to display the operative field image in the display screen with reference to the determined target point, wherein the control of the mechanism is based on the generated parameter.

7. The input control device according to claim 6, wherein the parameter is for execution of at least one of:
a zoom control of a camera that captures the operative field image, or
a drive control of a camera arm that supports the camera.

8. An input control method, comprising
determining, by an input control device, one of:
a user's line-of-sight position with respect to an operative field image matches with a characteristic point in the operative field image, or
the user's line-of-sight position is different from the characteristic point in the operative field image,
wherein the operative field image is displayed on a display screen;
determining, by the input control device, the user's line-of-sight position as a target point, wherein
the target point is a display reference for the operative field image displayed in the display screen, and
the user's line-of-sight position is determined as the target point based on the determination that the user's line-of-sight position with respect to the operative field image is different from the characteristic point in the operative field image; and
controlling, by circuitry, movement of the determined target point in the operative field image to a center of the display screen.

9. An operation system, comprising:
a camera configured to capture an operative field image;
a display screen configured to display the operative field image;
an input control device that includes a target point determination unit and circuitry that determines wherein
the target point determination unit is configured to:
determine one of:
a user's line-of-sight position with respect to the operative field image matches with a characteristic point in the operative field image, or
the user's line-of-sight position is different from the characteristic point in the operative field image,
wherein the operative field image is displayed on the display screen; and
determine the user's line-of-sight position as a target point, wherein
the target point is a display reference for the operative field image displayed in the display screen, and
the user's line-of-sight position is determined as the target point based on the determination that the user's line-of-sight position with respect to the operative field image is different from the characteristic point in the operative field image; and
the circuitry is configured to control movement of the determined target point in the operative field image to a center of the display screen.

* * * * *